United States Patent [19]

McGowan

[11] 4,258,440
[45] Mar. 31, 1981

[54] CLOTHES FOR THE PHYSICALLY HANDICAPPED

[76] Inventor: Malissa McGowan, 1502 E. 126th St., Compton, Calif. 90222

[21] Appl. No.: 907,740

[22] Filed: May 19, 1978

[51] Int. Cl.² ............................ A41B 1/10; A41D 1/06
[52] U.S. Cl. ............................................ 2/114; 2/227; 2/238; 2/403; 2/DIG. 7
[58] Field of Search ................... 2/227, 228, 108, 114, 2/DIG. 7, 403, 406, 83, 74, 238, DIG. 6

[56] References Cited

U.S. PATENT DOCUMENTS

| 2,201,662 | 5/1940 | DeLuco | 2/227 X R |
| 2,504,534 | 4/1950 | Kephart et al. | 2/114 |
| 2,722,686 | 11/1955 | Hoskings | 2/74 |
| 2,923,009 | 2/1960 | Cookman | 2/227 |
| 3,266,057 | 8/1966 | Phelps | 2/227 |
| 3,276,036 | 10/1966 | Cater | 2/74 |
| 3,800,330 | 4/1974 | Bowcut | 2/227 |
| 4,068,315 | 1/1978 | Rainville | 2/114 |

FOREIGN PATENT DOCUMENTS

| 512028 | 6/1952 | Belgium | 2/406 |
| 620555 | 3/1949 | United Kingdom | 2/406 |

*Primary Examiner*—H. Hampton Hunter
*Attorney, Agent, or Firm*—Louis J. Bachand

[57] ABSTRACT

Provided is a garment adapted for wear by physically handicapped persons who are incapable of executing normal dressing movements. The garment comprises a front panel applicable to the front of the handicapped person's torso and a rear panel applicable to the back of said person's torso. The front and rear panels each have opposed side edge margins and fastening means distributed thereon for simultaneously assembling and securing the garment to the wearer's torso by interconnecting the front and rear panel along their opposing edge margins in torso supported relation in the worn condition of the garment, without the necessity of normal dressing movement.

6 Claims, 4 Drawing Figures

U.S. Patent     Mar. 31, 1981     4,258,440
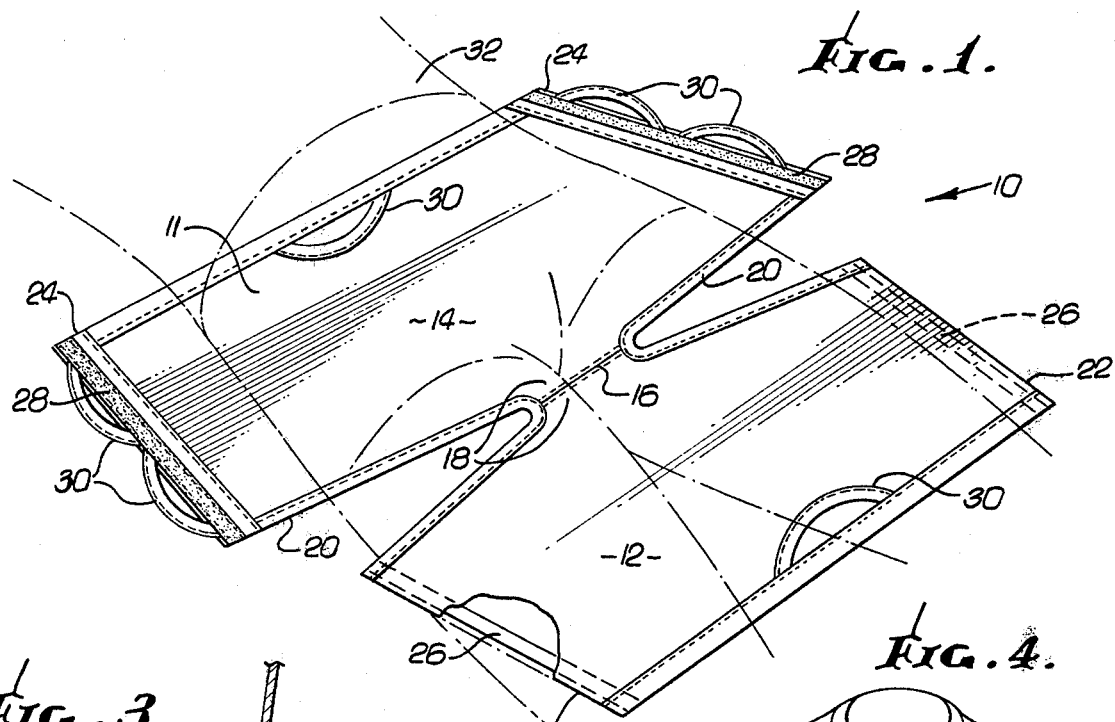
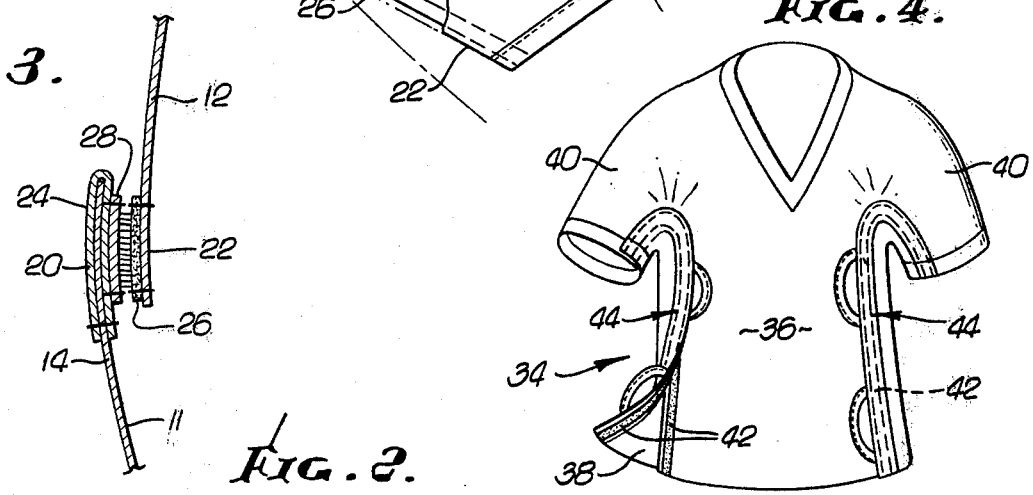
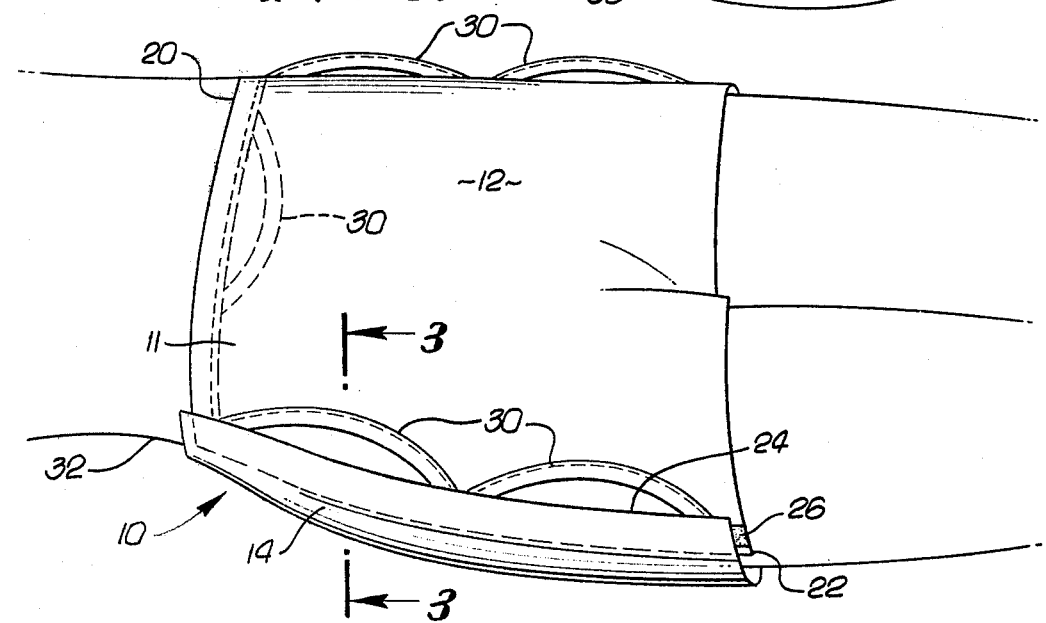

CLOTHES FOR THE PHYSICALLY HANDICAPPED

BACKGROUND OF THE INVENTION

This invention is related to novel garment assembly especially useful for the physically handicapped person, and more particularly the invention relates to garments for the physically handicapped which are provided in separable panels assemblable on the wearer's body so that there is no need to execute the normal dressing movements such as folding the legs and arms.

Those who are physically handicapped through stiffness of joints or through absence of all or part of the limbs often find it difficult to don garments of conventional design. Because such persons are unable to either fold their arms or fold their legs for purposes of inserting the limb into the conventional garment opening, they are frustrated in their efforts to wear conventional apparel and must have others assist them in dressing.

Actually, this is a burden on those living with handicapped persons and as the ensuing description will reveal, an unnecessary burden. The difficulty of donning a conventional garment when one is handicapped can perhaps best be visualized by attempting to put on a pair of pants or a shirt or blouse without folding the leg or arm. It immediately becomes evident that without folding of the limbs, the leg for example, the arms are simply not long enough to permit the insertion of the leg into the pants. There are numerous handicapped persons who face this difficulty each day which contributes to their feeling of helplessness and inability to cope with the outside world.

SUMMARY OF THE INVENTION

It is accordingly a major objective of the present invention to provide clothing which, while conventional in appearance, is unconventionally constructed so as to enable facile donning thereof by the handicapped person. It is a more particular object of the invention to provide clothing which can be assembled on the torso of the wearer without need for executing normal dressing movements.

It is another and further object of the invention to provide means for readily grasping the presently provided garments to better enable the donning thereof by a handicapped person.

These and other objects of the invention to become apparent hereinafter, are achieved in accordance with the teachings hereof, by a garment adapted for wear by a physically handicapped person incapable of executing normal dressing movement wherein the garment comprises a front panel, applicable to the front of the person's torso, and a rear panel applicable to the back of the person's torso, the front and rear panels having opposed side edge margins and distributed fastening means thereon for simultaneously assembling and securing the garment to the wear's torso by interconnecting the front and rear panels along their opposed edge margins in torso supported relation in the worn condition of the garment and without the necessity of normal dressing movements.

In particular embodiments, the mentioned panels are front and rear pant panels and the invention further includes a crotch portion extending adjacently below the torso between panels in pant completing relation. Alternatively, the panels may be front and rear shirt panels having sleeve segments, and further include additional fastening means disposed along the length of the segments for completing a sleeve about the arm of the person in the worn condition. The garment panels typically formed of fabric may have fastening means which comprise longitudinally extended pressure responsive mechanical interconnectors such as Velcro connectors secured to opposing edge margins of the panels in garment defining relation.

As mentioned above, as a further feature of the invention, there is provided means facilitating handling of the garment by the handicapped, which means comprise hand receiving loops attached to the panels in edge margin positioning relation thereby to facilitate application of the front and rear panels to the person's torso for garment assembly.

Accordingly then, in the more preferred embodiments of this invention, the garment comprises panels which are front and rear pant panels having side seams defined by opposing panel edge margins overlapping in fastener secured relation to be separable by drawing on the loops, and further including also a crotch portion extending adjacently below the torso between panels, again in pant completing relation. In the shirt embodiment the panels are front and rear shirt panels having sleeve segments and include also additional fastening means disposed along the length of the segments for completing the sleeve about the arm of the person in the worn condition of the garments. Such additional fastening means typically will comprise longitudinally extended pressure responsive mechanical interconnectors, e.g. Velcro, disposed along the length of the segments in opposed relation.

BRIEF DESCRIPTION OF THE DRAWINGS

The invention will be further described as to illustrative embodiment in conjunction with the attached drawings in which:

FIG. 1 is a plan view of a pant embodiment of the present invention shown open prior to assembly, with a torso superimposed thereon for clarity of understanding;

FIG. 2 is a perspective view of the garment shown in FIG. 1 in the assembled condition of the garment, the assembly loops being shown for clarity of understanding;

FIG. 3 is a view in horizontal section taken on line 3—3 in FIG. 2; and

FIG. 4 is a perspective view of a shirt embodiment of the invention.

DESCRIPTION OF THE PREFERRED EMBODIMENT

With reference now to the drawings in detail, in FIG. 1 a garment pant embodiment is depicted at 10, shown open, as prior to assembly. Thus, cloth or fabric 11 is cut into an approximate rectangle to define a front panel 12 and a second rectangle to define a rear panel 14. The size and specific shape of the panels 12, 14 are dictated by style and clothing size requirements and considerations. The front and rear panels 12, 14 are sewn together at 16, the surrounding region 18 defining a crotch portion which may be a separate section (not shown) or continuations of the respective panels, as shown. A conventional bias tape 20 is provided around the parameter of the garment 10. The edge margins 22, 24 of panels 12, 14 respectively, carry a longitudinally distributed mechanical fastener, 26,28, e.g. Velcro, or other type of generally continuous fastener device, which is sewn or otherwise secured to these edge margins so that pressing together or other contact of the opposed edge margins (see FIG. 3) will effect engagement of the fasteners and thus couple their respective edge margins together. Further shown and beyond the fastener 26, are loops 30 which are hand receiving for ease of manipulation of the garment panel, e.g. 14.

The garment 10 is donned as indicated in FIG. 1 by the person sitting or lying atop rear panel 14 with the person's torso 32 in approximate registration with the garment thereunder. Similarly, where the garment is a coveralll consisting of pants and shirt joined together or only a shirt as shown in FIG. 4 the pant rear panel 14 would underlie the buttocks, a shirt rear panel such as 38 in FIG. 4 would underlie the back and shoulders, and so on.

With the torso 32 thus approximately positioned, the wearer draws the rear panel 14 side edge margins 24 in about the hips by the loops 30 and folds the front panel 12 through the legs and then spreads the front panel so that its edge margins 22 are opposite and overlain by the rear panel edge margins 24, and the e.g. Velcro, fastener portions 26 thereon are in registry (See FIG. 3); the fastener portions then being pressed together to effect an interconnection of the garment panels 12, 14, and assembly of the garment shown in FIG. 2. The loops 30 are normally folded back out of view under the connected panels but are shown, for purposes of clarity in FIG. 2, where they would be in the assembled condition of the garment if the loops were not so folded back.

An outstanding feature of the loops 30 is that the garment can be pulled up or around the body, arms, etc., even though the wearer may not have flexibility in the fingers or hands. That is, it is not necessary to have digital grasping of the garment edges.

The shirt or blouse 34 (FIG. 4) is similarly assembled on the torso and from corresponding front and rear panels 36, 38 with sleeves 40 having like longitudinal fasteners 42 along their seam regions 44.

It will be evident from consideration of the foregoing, that useful garments, in a wide variety of styles can now be made available to the physically handicapped, for donning without need of inserting leg and/or arm through conventional leg or arm holes, all to the greater convenience and comfort of the wearer and those normally assisting them.

Thus, a nurse or attendant may apply the garment without lifting the patient; rolling the patient left and right will allow application of garment to the patient without lifting of the torso or extremities.

The above described embodiments of this invention are merely descriptive of its principles and are not to be considered limiting. The scope of this invention instead shall be determined from the scope of the following claims including their equivalents.

What is claimed is:

1. Garment adapted for wear by a physically handicapped person incapable of executing normal dressing movements;

said garment comprising a front panel applicable to the front of the said person's torso, a rear panel applicable to the back of said person's torso, said front and rear panels having opposed side edge margins and distributed fastening means thereon for simultaneously assembling and securing the garment to the wearer's torso by interconnecting said front and rear panels along their opposed edge margins in torso supported relation in the worn condition of the garment, and loops sized to be hand receiving attached to said panels co-distributively with said fastening means along the panel side edge margins in positioning relation to facilitate application of said front and rear panels to the person's torso by hand thrusting throught the loops to manipulate the garment panels into justaposition for garment assembly in wrapped relation about the person and without need of digital grasping of said panels and without the necessity of normal dressing movements.

2. Garment according to claim 1 in which said panels are front and rear pant panels and including also a crotch portion extending adjacently below the torso between said panels in pant completing relation.

3. Garment according to claim 1 in which said panels are front and rear shirt panels having sleeve segments, and including also additional fastening means disposed along the length of said segments for completing a sleeve about the arm of the person in the worn condition of the garment.

4. Garment according to claim 1 in which said panels are formed of fabric.

5. Garment according to claim 4 in which said fastening means comprise:

longitudinally extended pressure responsive mechanical interconnectors secured to opposing edge margins of said panels in garment defining relation.

6. Garment according to claim 1 in which said panels are front and rear pant panels having side seams defined by opposed panel edge margins overlapping in fastener secured relation to be separable by drawing on said loops, and including also a crotch portion extending adacently below said torso between panels in pant completing relation.

* * * * *